United States Patent [19]
O'Boyle

[11] Patent Number: 5,609,606
[45] Date of Patent: Mar. 11, 1997

[54] ULTRASONIC ANGIOPLASTY BALLOON CATHETER

[75] Inventor: Matthew O'Boyle, Webster, Tex.

[73] Assignee: Joe W. & Dorothy Dorsett Brown Foundation, New Orleans, La.

[21] Appl. No.: 481,184

[22] Filed: Jun. 7, 1995

Related U.S. Application Data

[63] Continuation of Ser. No. 14,021, Feb. 5, 1993, abandoned.

[51] Int. Cl.⁶ .................................................. A61B 17/00
[52] U.S. Cl. ........................ 606/194; 606/191; 606/171; 606/169; 604/22
[58] Field of Search ........................ 606/159, 169–171, 606/191, 192, 194; 604/20, 22

[56] References Cited

U.S. PATENT DOCUMENTS

| | | |
|---|---|---|
| 2,615,865 | 10/1952 | Gilbert et al. . |
| 2,615,866 | 10/1952 | Gilbert et al. . |
| 2,615,867 | 10/1952 | Gilbert et al. . |
| 2,615,868 | 10/1952 | Miller . |
| 2,615,869 | 10/1952 | Folt . |
| 2,615,870 | 10/1952 | Folt . |
| 2,615,871 | 10/1952 | Folt . |
| 2,615,872 | 10/1952 | Averill . |
| 2,615,873 | 10/1952 | Averill . |
| 2,615,874 | 10/1952 | Gilbert et al. . |
| 2,615,875 | 10/1952 | Gilbert et al. . |
| 2,615,876 | 10/1952 | Gilbert et al. . |
| 2,615,877 | 10/1952 | Folt . |
| 2,615,878 | 10/1952 | Folt . |
| 2,615,879 | 10/1952 | Folt et al. . |
| 2,615,880 | 10/1952 | Folt . |
| 2,628,954 | 2/1953 | Gilbert . |
| 2,650,911 | 9/1953 | Gilbert et al. . |
| 2,654,728 | 10/1953 | Gilbert et al. . |
| 2,657,197 | 10/1953 | Carlson . |
| 2,716,104 | 8/1955 | Gilbert et al. . |

(List continued on next page.)

FOREIGN PATENT DOCUMENTS

| | | |
|---|---|---|
| 569262 | 1/1959 | Canada . |
| 189329 | 7/1986 | European Pat. Off. ................ 606/194 |
| 205081 | 12/1986 | European Pat. Off. ........ A61M 25/00 |

OTHER PUBLICATIONS

American Heritage Dictionary p. 67, definition of "ablation".

Fischell, T. A., et al., "Ultrasonic Energy, Effects on Vascular Function and Integrity", Circulation, vol. 84, No. 4, pp. 1783–1795. Oct. 1991.

Siegal, R. J., et al., "Percutaneous peripheral ultrasonic angioplasty: Results of the first pilot study and follow–up", Herz, 15:5, pp. 329–334 (1960).

(List continued on next page.)

Primary Examiner—David M. Shay
Attorney, Agent, or Firm—Fitch, Even, Tabin & Flannery

[57] ABSTRACT

An angioplasty balloon catheter particularly adapted for ablation of a stenosis in vivo has a balloon which may be inflated with a conductive contrast fluid injected proximally to the balloon, and is furthermore metalized on the outside of the balloon and catheter shaft. The balloon has piezoelectric properties, and may be excited by application of an ultrasonic signal across the balloon between the metalized surface and the contrast fluid. The catheter is guided by a centrally located guide wire to the site of the stenosis. If the distal tip of the catheter shaft cannot pass through the stenosis, excitation of the piezoelectric balloon in a deflated state at the site of the stenosis causes ultrasonic hammering vibrations at the tip of the catheter shaft which ablate the stenosis. After the tip of the catheter has hammered its way across the stenosis, and while maintaining the ultrasonic excitation signal, the balloon is inflated to keep the vibrating balloon surface in contact with the stenosis. Unlike the case with other inflatable balloon catheters which simply press the stenosis against the blood vessel wall, the stenosis is broken up by ultrasonic vibrations and is carried away by the blood flow, minimizing the risk of re-stenosis.

29 Claims, 4 Drawing Sheets

U.S. PATENT DOCUMENTS

| | | |
|---|---|---|
| 2,716,105 | 8/1955 | Gilbert et al. . |
| 2,716,106 | 8/1955 | Gilbert et al. . |
| 2,740,769 | 5/1956 | Gilbert et al. . |
| 3,506,991 | 5/1970 | Adams, Jr. et al. . |
| 4,490,421 | 12/1981 | Levy . |
| 4,522,194 | 6/1985 | Normann .................................. 600/16 |
| 4,637,401 | 1/1987 | Johnston . |
| 4,638,287 | 1/1987 | Radice .................................. 310/328 |
| 4,674,336 | 6/1987 | Johnston . |
| 4,698,058 | 10/1987 | Greenfeld et al. . |
| 4,802,490 | 2/1989 | Johnston . |
| 4,841,977 | 6/1989 | Griffith et al. . |
| 4,843,275 | 6/1989 | Radice .................................. 310/334 |
| 4,869,263 | 9/1989 | Segal et al. . |
| 4,878,898 | 11/1989 | Griffin et al. . |
| 4,889,128 | 12/1989 | Millar . |
| 4,911,170 | 3/1990 | Thomas et al. . |
| 4,920,967 | 5/1990 | Cottonaro et al. . |
| 4,951,677 | 8/1990 | Crowley et al. . |
| 4,957,111 | 9/1990 | Millar . |
| 4,991,588 | 2/1991 | Pflueger et al. . |
| 5,009,662 | 4/1991 | Wallace et al. . |
| 5,046,503 | 9/1991 | Schneiderman . |
| 5,076,268 | 12/1991 | Weber . |
| 5,109,861 | 5/1992 | Walinsky et al. . |
| 5,112,347 | 5/1992 | Taheri . |
| 5,135,001 | 8/1992 | Sinofsky et al. . |
| 5,443,495 | 8/1995 | Buscemi et al. .................. 606/191 |

OTHER PUBLICATIONS

Barry, K. J., et al., "The effect of radiofrequency–generated thermal energy on the mechanical and bioplasty characteristics of the arterial wall in vivo: Implications for radiofrequency angioplasty", American Hear Journal, vol. 117, No. 2, pp. 332–341 (Feb. 1989).

Siegel, R. J., et al., "Percutaneous Ultrasonic Angioplasty: Initial Clinical Experience", The Lancet, pp. 772–774, Sep. 30, 1989.

Avedissian, M. G., et al., "Percutaneous Transluminal Coronary Angioplasty: A Review of Current Balloon Dilation Systems", Catheterization & Cardiovascular Diagnosis, 18:263–275 (1989).

Langberg, J. J., et al., "The Echo–Transponder Electrode Catheter: A New Method for Mapping the Left Ventricle", J. Amer. Col. Cardiology, vol.. 12, No. 1, pp. 218–223 (Jul. 1988).

Barzilai, B., et al., "Quantitative Ultrasonic Characterization of the Nature of Atherosclerotic Plaques in Human Aorta", Circulation Research, vol. 60, No. 3, pp. 459–463 (Mar. 1987).

Reder, G. S., and Vliestra, R. E., "Coronary Angioplasty: 1986", Modern Concepts of Cardiovascular Disease, vol. 55, No. 10, pp. 49–53 (Oct. 1986).

Martin, R. W., and Watkins, D. W., "An Ultrasonic Catheter for Intravascular Measurement of Blood Flow: Technical Details", IEEE Trans. Sonics & Ultrasonics, vol, SU–27, No. 6, pp. 277–286 (Nov. 1980).

Cole, J. S., and Hartley, C. J., "The Pulsed Doppler Coronary Artery Catheter: Preliminary Report of a New Technique for Measuring Rapid Changes in Coronary Artery Flow Velocity in Man", Circulation, vol. 56, No. 1, pp. 18–25 (Jul. 1977).

Hartley, C. J., and Cole, J. S., "An ultrasonic pulsed Doppler system for measuring flood flow in small vessels", J. Applied Physiology, vol. 37, No. 4, pp. 626–629 (Oct. 1974).

Benchimol, A., et al., "Aortic flow velocity in man during cardiac arrhythmias measured with the Doppler catheter–flowmeter system", American Heart Journal, vol. 78, No. 5, pp. 649–659 (Nov. 1969).

American Edwards Laboratories Percutaneous Transluminal Angioplasty Catheters, "User's Reference Guide for Peripheral Applications", Brochure, unknown publication date.

Liaw, C. F., and Chen, I. C., "Poling of Multiple PVDF Films by Moving Corona Discharge", Ferroelectrics, vol. 99, pp. 127–132 (1989).

Carlisle, B. N., "Piezoelectric Plastics Promise New Sensors", unknown journal, Penton Publishing, 1986.

Schonhorn, H., and Hansen, R. H., "Surface Treatment of Polymers for Adhesive Bonding", Journal of applied Polymer Science, vol. 11, pp. 1461–1474 (1967).

Benderly, A. A., "Treatment of Teflon to Promote Bondability", Journal of Applied Polymer Science, vol. 6, No. 20, pp. 221–225 (1962).

ULTRASONIC ANGIOPLASTY BALLOON CATHETER

This application is a continuation of application Ser. No. 08/014,021 filed Feb. 5, 1993, now abandoned.

BACKGROUND OF THE INVENTION

The invention broadly relates to a catheter and a method for its use in opening a stenosis in a coronary artery or any other vascular vessel. In particular, the invention relates to an inflatable balloon catheter wherein the balloon also serves as a piezoelectric generator of ultrasonic energy for breaking up the stenosis.

Percutaneous transluminal angioplasty (PTA) is presently the primary therapy for certain forms of atherosclerotic artery disease. The major application of the procedure is in the coronary arteries, but the procedure can also be used in peripheral arteries or any vascular vessel. Atherosclerosis results in the restriction and blockage of blood flow in arteries by an accumulation in the blood vessel of a variety of biological materials. Such restriction or blockage results in oxygen deprivation of the tissue supported by the blood supply. This deprivation and its effect, angina, is referred to as "ischemia". If the blood supply through the coronary artery is almost completely or completely blocked for more than two or three minutes, permanent damage to the myocardia or infarction and death may result. The biological matter causing arterial blockage (stenosis) may be plaque, or thrombotic, calcific or fibrous matter or any combination thereof.

Several methods are known in the art to dilate an existing path through a stenosis and restore blood flow. Balloon angioplasty requires the insertion into the blood vessel and through the stenosis of a deflated balloon, which is hydraulically inflated to stretch and compact the stenosis material against the wall of the artery. This procedure is somewhat effective; however, the incidence of re-stenosis is high, and in many cases by-pass surgery must be undertaken. A confirmed attendant risk associated with this procedure is subsequent downstream embolism or clogging, which can be essentially as serious as the most serious stenosis which the procedure is designed to remedy.

In order that the smallest possible stenosed aperture may be crossed, conventional balloon catheter designs call for a balloon having minimal profile diameter in the deflated state. As a result, the balloon wall thickness must be minimized, reducing the burst pressure of the balloon. At the same time, however, there is a growing demand for higher balloon burst pressures to overcome the high resistance of some biological materials in stenoses that are somewhat or completely calcified.

The need for a minimal profile diameter in the deflated state also requires a minimization of the catheter shaft tip to as small a diameter as can accommodate a given guide wire. However, this impairs the pushability of the catheter across the stenosis, since a thinner shaft is also a weaker shaft.

Most balloons are made of either polyethylene, polyethylene terephthalate (PET), or a polyolefin copolymer. A conventional balloon catheter comprises a balloon-over-a-wire design, however this invention anticipates on-the-wire piezoelectric catheters where the guide wire occupies a central lumen of the catheter.

A recent development in treatment of stenosis is the use of ultrasonic energy to break up the biological material comprising stenosis in peripheral blood vessels. The mechanisms of ultrasound treatment are primarily direct mechanical effects and cavitation. Generally, the ultrasonic energy is generated in vitro and delivered, for example, via a titanium wire of 0.5 millimeter diameter to the 2 millimeter spherical tip of the catheter at the site of stenosis. Frequencies in the range of 10–20 kHz are typically used with a power output of up to 20–25 W/cm$^2$. Such a device is described in R. J. Siegel et al., "Percutaneous Ultrasonic Angioplasty: Initial Clinical Experience", Lancet pp 772–774, Sep. 30, 1989.

The spherical tip must be large enough to create a pathway through the stenosis through which a subsequent angioplasty balloon catheter may pass. Unfortunately, though the spherical tip breaks open a lumen of approximately 2 millimeter diameter through the stenosis, it does not remove the annulus of biological material which surrounds the 2 mm aperture. Instead the annulus must be crushed against the vessel wall by the subsequent angioplasty balloon in order to achieve a larger aperture.

Another problem with the conventional catheters used to mechanically deliver ultrasonic energy is that the titanium wire which is generally used for this purpose is relatively stiff and therefore cannot be effectively steered into a coronary artery. A thinner, more flexible wire, such as stainless steel, is not able to transmit effectively the amount of ultrasonic energy required by the procedure. Titanium is thus the material of choice in the mechanical transmission of the ultrasonic energy. Consequently, this method of delivering ultrasonic energy for ablation of the stenosis cannot be applied to the coronary arteries.

Diagnostic catheters are known in the art which have in vivo piezoelectric transducers at their tips. These piezoelectric transducers are used for ultrasonic imaging of the vessel in which the catheter is inserted. Often, such transducers are used in combination with an angioplasty balloon catheter. In such a combination, the transducer provides imaging of the stenosis for which the balloon is used to dilate. The transducer may also be used to measure the flow in an autoperfusion catheter, in which a conduit is incorporated in the catheter to allow blood to flow by the inflated balloon. Such a catheter is disclosed in U.S. Pat. No. 5,046,503 to Schneidermann. The piezoelectric transducer is a piezoelectric crystal placed adjacent the autoperfusion conduit inside the balloon.

A different kind of piezoelectric element can be found in the intravascular, ultrasonic imaging catheter of U.S. Pat. No. 5,109,861 to Walinsky et al. Thin layers of flexible plastic material, such as polyvinylidene diflouride (PVDF), are utilized which can be spot polarized in active regions to exhibit piezoelectric characteristics. This kind of imaging catheter may be used in conjunction with balloon catheters to assist in locating the portion of the vessel wall to be treated. However, the low amplitude, high frequency piezoelectric transduction of ultrasonic energy cannot, and is not intended to, ablate the stenosis under observation.

U.S. Pat. No. 5,135,001 discloses a piezoelectric element in the form of a PVDF layer sandwiched between an inner cylindrical electrode and a plurality of outer electrode strips running axially along the length of the catheter, for use in imaging the inside surface of the blood vessel. In one embodiment, the piezoelectric element is contained within an inflatable balloon. After the catheter is positioned at the desired location, the balloon may be inflated with liquid until it contacts the vessel walls. This assures more efficient transmission and echo reception of ultrasound energy than would be possible if there were gaps between the catheter sheath and the vessel walls. In alternative embodiments, the outer electrode strips are located on the outer surface of the balloon, while the balloon still contains the inner cylindrical electrode and the piezoelectric layer. The electrode strips may also be attached to the inside of the inflatable balloon.

While it has been demonstrated that ultrasonic energy can be used to image the inside surfaces of blood vessels, and ultrasonic energy has been delivered over titanium wires to stenoses in peripheral vessels to open up a nominal aperture, no effective means of delivering ultrasonic energy to substantially ablate stenosis material in a coronary artery as provided by the present invention is presently available. There is a need for a catheter which can deliver ultrasonic energy to the location of stenosis, to substantially open the blockage without the need to use balloon pressure to crush the stenosis open. There is a further need to avoid the high risk of re-stenosis which accompanies balloon angioplasty, and to ablate the stenosis material in particle sizes sufficiently small to reduce the risk of downstream embolism.

SUMMARY OF THE INVENTION

It is an object of the present invention to provide an angioplasty balloon catheter, and a method for its use, which has a piezoelectric balloon capable of delivering sufficient in vivo ultrasonic energy for ablating biological material comprising a stenosis of coronary arteries or other blood vessels in the human body. It is a further object of the present invention to provide a catheter wherein the piezoelectric balloon may be excited to deliver ultrasonic energy in either the deflated or inflated state, or any state of partial inflation with a contrast fluid.

The catheter has a lumen through which a guide wire may be passed for guiding the catheter to the site of stenosis. The catheter further has at its distal end a balloon preferably comprising a polyvinylidene diflouride (PVDF) homopolymer or crosslinked with a polyolefin copolymer, which has been poled by corona discharge such that it exhibits piezoelectric properties. The balloon may be inflated via other lumens in the catheter with a contrast fluid which is electrically conductive. The outer shaft of the catheter, as well as the outer surface of the balloon, are metalized to provide a conductive path on the outside of the catheter. An ultrasonic frequency signal may be applied between the outer metalized surface and the conductive contrast fluid to excite the piezoelectric balloon into ultrasonic vibratory states.

According to the method of the invention, the catheter is guided to the site of arterial stenosis by means of a guide wire. If the stenosis is complete, such that the catheter cannot be pushed across the stenosis, an excitation signal may be applied to the balloon in its deflated state, which causes a longitudinal vibratory motion, in effect hammering the tip of the catheter through the biological material of the stenosis.

When the catheter has crossed the stenosis, the balloon may be inflated while the excitation signal is maintained. The inflation of the balloon causes the vibrating surface of the balloon to remain in mechanical contact with the stenosis material, and the stenosis is further ablated. The inflation of the balloon does not predominantly cause a crushing of the material of the stenosis against the vessel wall, but rather maintains intimate contact between the material and the vibrating surface, thereby maximizing delivery of ultrasonic energy to the material, and causing its complete ablation. Repeated inflations and deflations of the balloon allow for flushing of the ablated material by perfusion of blood.

The guide wire may be chosen to have a flexibility such that the catheter and guide wire may be steered into and used in coronary arteries.

DESCRIPTION OF THE PREFERRED EMBODIMENT

Generally, the catheter of the present invention comprises an tubular extrusion having at least two lumen. A first lumen is used to accommodate a flexible guide wire. A second lumen forms a fluid path for a conductive contrast fluid which both serves to inflate a balloon located at the distal end of the catheter, and to conduct an ultrasonic electrical signal. The outer surface of the catheter is metalized along its length, as is the outer surface of the balloon at its distal end, to form a second conductive path for the application of an ultrasonic electrical signal. The balloon is formed of polymeric material having piezoelectric properties. The outer metalized surface forms one conductive path to the outer surface of the balloon, while the conductive contrast fluid forms a second conductive path to the inner surface of the balloon, such that an ultrasonic signal across the two conductive paths creates a signal potential across the material thickness of the balloon. By virtue of its piezoelectric properties, the balloon will mechanically deform in response to the changing potential. At the proximal end of the catheter, an appropriate hub or connector facilitates connection to a source of contrast fluid and to a source of ultrasonic electrical signal.

Figure 1:
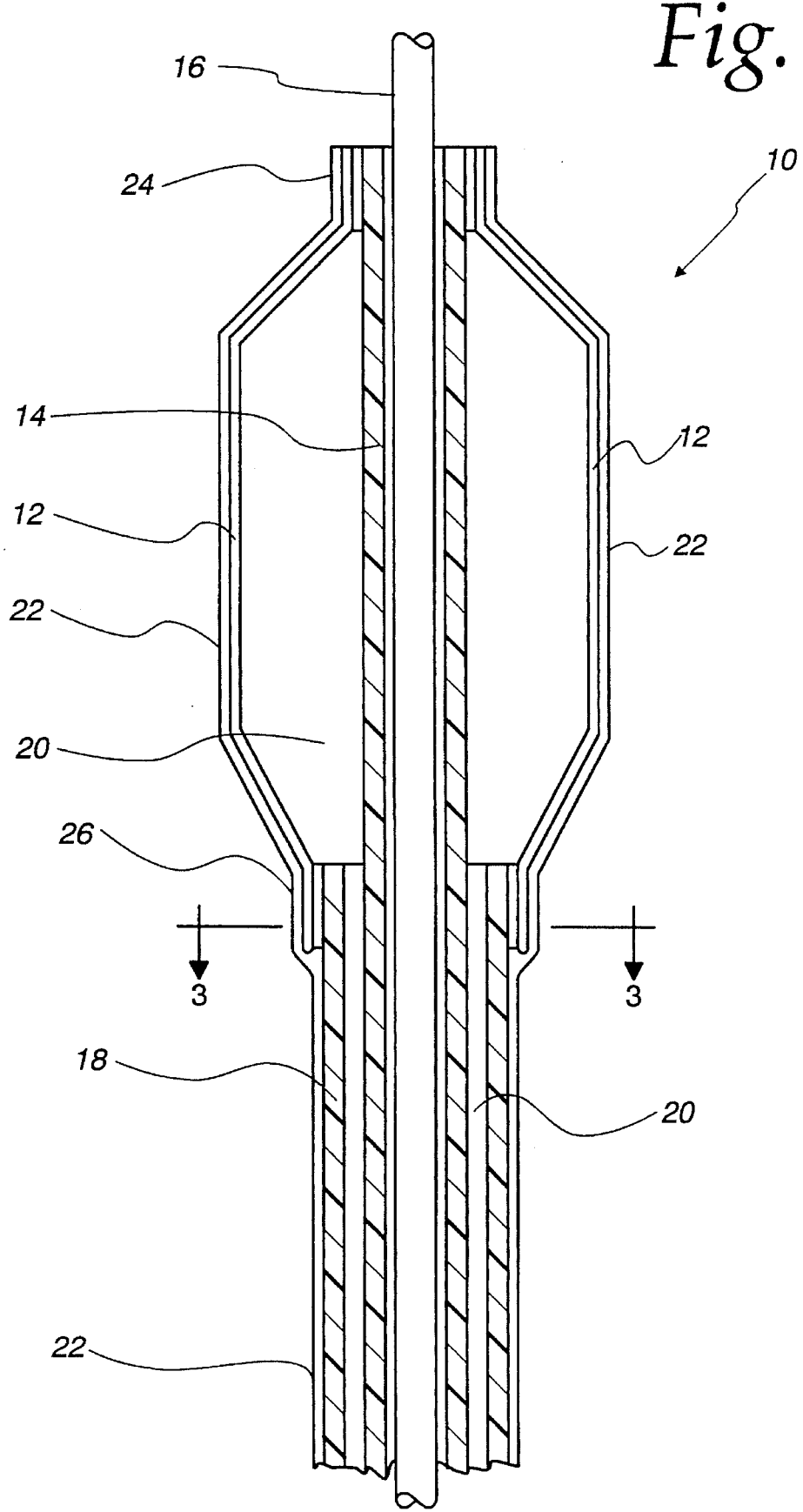
FIG. 1 is a long-sectional view of the distal end of the preferred embodiment of the catheter of the present invention.

Turning to FIG. 1, the distal end 10 of a catheter according to the present invention has an angioplasty balloon 12 which also acts as a transducer when excited by a.c. or d.c. frequencies of up to 1 GHz. One end of the balloon is connected to an inner tube 14 of the catheter, which tube serves as the through-hole for the guide wire 16. At its other end, the balloon is connected to the outer tube 18 of the catheter. The space between the inner tube 14 and the outer tube 18 defines a fluid path 20 into which a conductive contrast fluid may be pumped to provide an inflation pressure for the balloon, and additionally to provide a conductive path for the application of an excitation signal to the piezoelectric balloon. A second conductive path takes the form of a layer 22 of metalization which covers the outer surface of the balloon and the outer surface of the outer tube 18. The metalization layer 22 preferably does not contact any portion of the inner tube 14.

The balloon may comprise a flexible, expandable polymeric material possessing piezoelectric properties. Many well-known materials are suitable, such as a copolymer synthesized from polyvinylidene difluoride (PVDF)/trifluoroethylene crosslinked with a polyolefin polymer. Such a balloon may be readily fabricated as is known in the art from extruded tubing, with inflated dimensions preferably approximately in the range of 2 mm to 4 mm in diameter, and a length approximately in the range of 20 mm to 25 mm, depending upon the desired application. The wall thickness preferably should be approximately in the range of 9 microns to 56 microns, however, for a given balloon size, the capacitance will vary with the wall thickness, and may need to be taken into consideration.

The tensile strength of piezoelectric homopolymers, copolymers and compounds is only approximately half that of polyethylene terephthalate (PET), which is commonly used for fabrication of conventional angioplasty balloons. However, high inflation pressures typically required of conventional angioplasty balloons are not required in the present invention, because the inflation of the balloon according to the present invention is not primarily for the purpose of crushing the stenosis material against the vessel wall, but rather primarily for merely maintaining contact between the balloon surface and the stenosis material as the stenosis is ablated.

The extrusion of such balloons is known in the art, such as in U.S. Pat. No. 4,490,421 to Levy, the teachings of which are incorporated by reference. The method in Levy describes the formation of balloons from polyethylene terephthalate, but can be used identically in the formation of balloons from piezoelectric homopolymers, copolymers and compounds which can be bi-axially oriented, i.e., which can be blown after extrusion. Alternatively, custom fabricated balloons are commercially available from such companies as Advanced Polymers, Inc., of Salem, N.H.

Piezoelectric copolymers are typically long-chain semicrystalline polymers containing repeating units of $CH_2$—$CF_2$. By way of example, PVDF may be compounded with PET in a ratio of 30% to 70% by dry weight to produce a piezoelectric material which can be bi-axially oriented. Such a compound may be prepared by extruding the 70 parts-by-weight of 5-micron granulated PVDF, then pelletizing the extrusion, and mixing with the 30 parts-by-weight of granulated PET, and extruding, stretching and blowing the mixture to form a balloon from the resulting compound, which can be subsequently treated to create piezoelectric properties, as outlined below.

Alternatively, PET may be compounded with the copolymer PVDF/trifluoroethylene, which has a piezo-constant approximately twice that of PVDF alone. Yet another alternative is the compound of PET and the copolymer PVDF/tetrafluoroethylene. PET may also be compounded with polyvinylidene cyanide, which exhibits piezoelectric properties similar to those of PVDF. In each case, PET may be replaced by any suitable polyolefin copolymer, such as polyethylene/ethyl vinyl alcohol. A variety of piezoelectric materials may be used for the balloon, comprising one of any number of compounded and/or crosslinked combinations of at least one of the set of piezoelectric copolymers such as PVDF, polyvinylidene fluoride, PVDF/tri- and PVDF/tetra-fluoroethylene, and polyvinylidene cyanide, and at least one of the set of polyolefin copolymers like PET or polyethylene/ethyl vinyl alcohol.

According to the preferred embodiment of the invention, the piezoelectric balloon comprises a copolymer that is synthesized from PVDF/trifluoroethylene crosslinked and/or compounded with a suitable polyolefin copolymer, in a ratio that provides maximum piezoelectric response with the ability to be bi-axially oriented.

After extrusion and blowing, the balloon must be treated so that it exhibits piezoelectric properties. What is called the "alpha phase" of the material occurs when the polymer is cooled from a molten state. This phase is not piezoelectric. Typically, the exemplary piezoelectric material polyvinylidene diflouride (PVDF) may be converted to its potentially piezoelectric beta phase by a three-step treatment comprising physical stretching, electrical poling and electroding. In the present invention, stretching is achieved during production of the balloon according to the method described in Levy. Alternatively, stretching of the tubular balloon as it is extruded, or inflation at high pressure of the balloon after extrusion, will also suffice to convert it to the beta phase. In the beta phase, the carbon chains are aligned in parallel strips and planes.

Subsequent poling of the beta-phase PVDF material by corona discharge or field poling yields alignment of hydrogen and fluorine atoms to form aligned dipoles in the material and resultant piezoelectric properties. One method of poling comprises passing the balloon between two electrodes which create a corona discharge. However, the piezoelectric nature of the resultant balloon will not be uniform around its circumference. In a preferred method of poling, a thin, cylindrical first electrode is placed inside the tubular balloon, while a second cylindrical electrode is placed around the outside of the balloon, and a corona discharge is initiated and maintained for a period of time across the thickness of the balloon. The electrical and ambient parameters required for poling by corona discharge are known in the art, and are detailed in C. F. Liaw et al., "Poling of Multiple PVDF Films by Moving Corona Discharge", Ferroelectrics, Vol. 99, pp. 127–132 (1989), the teachings of which are incorporated by reference.

The guide wire 16 may be made of a suitable material such as stainless steel. Any number of conventionally available guide wires may be chosen for insertion into the guide wire lumen.

Figure 2:
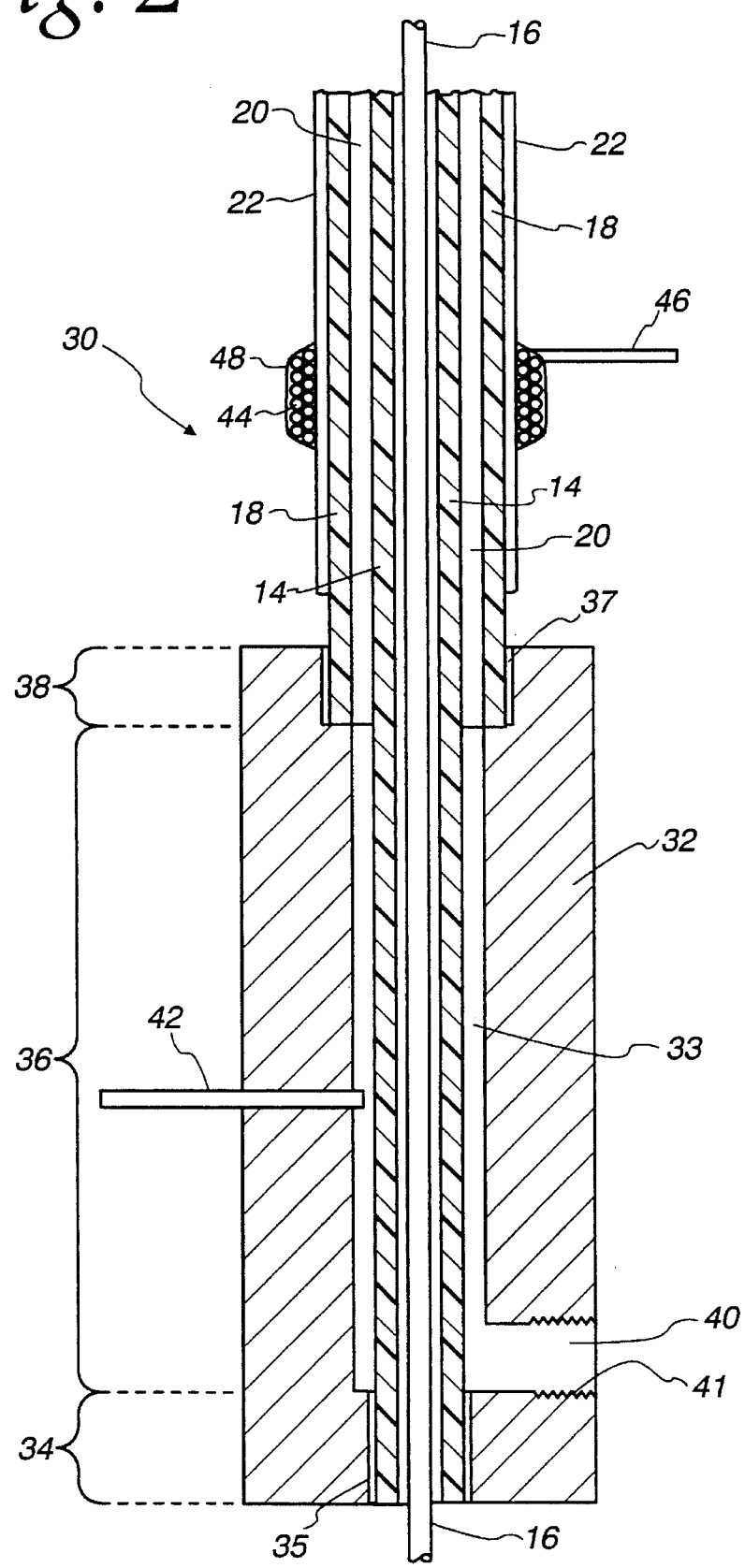
FIG. 2 is a long-sectional view of the proximal end of the preferred embodiment of the catheter of the present invention.

Turning now to FIG. 2, the proximal end 30 of the catheter according the present invention is shown having a catheter hub 32. A circular channel 33 through the length of the hub has three sections of differing diameters. A first section 34 has a channel diameter which can snugly accommodate adhesive bonding of inner tube 14 to its inner surface 35. A second section 36 has a channel diameter substantially greater than the outer diameter of inner tube 14, but smaller than the outer diameter of outer tube 18, to create a space around inner tube 14 for the flow of conductive fluid up the channel and into fluid pathway 20. A third section 38 has a channel diameter which can snugly accommodate adhesive bonding of outer tube 18 to its inner surface 37, as shown in FIG. 2. A bore hole 40 forms a pathway to the space of section 34 for the infusion of the conductive contrast fluid. The bore hole may have a winding 41 for the screw-like attachment or some other means of securing the attachment of a hose or pressure gauge or other device for delivering fluid to the fluid pathway 20 and sealing the fluid therein at a certain pressure. The hose or gauge may in turn connect to a mechanically or electrically controlled source of fluid pressure.

The hub 32 may be formed of polycarbonate, or any other polymeric material having approximately the same resilience, non-conductivity, and thermal and tensile qualities.

To provide for the application of an ultrasonic excitation signal to the piezoelectric balloon at the distal end of the catheter, a first electrically conductive lead 42 is embedded in hub 32 as shown in FIG. 2, such that one end protrudes from the hub to facilitate connection to a source of an ultrasonic electrical signal, and the other end protrudes into the fluid path between the hub channel diameter and the inner tube 14 outer diameter, such that it is in conductive contact with the fluid. The lead 42 is preferably a silver conductor. Furthermore, the lead 42 need not be limited to the short protrusion into the fluid path shown in FIG. 2, but may extend along the length of fluid pathway 20, all the way to the distal end of the catheter, entering the balloon void, thus reducing the impedance of the fluid path.

A second lead takes the form of a silver wire winding 44 wound around and in intimate conductive contact with the metalized surface of the outer tube 18, as shown in FIG. 2. A tail 46 of the wire winding facilitates electrical connection to a source of an ultrasonic electrical signal. The winding 44 is embedded in and surrounded by a bead 48 of conductive epoxy resin. A suitable conductive epoxy resin for this purpose, by way of example, is Tracon Tra-Duct 2922, available from Tracon, Inc., of Medford, Mass.

Importantly, the metalization layer 22 on the outer surface of outer tube 18 does not reach the catheter hub 32.

The inner tube 14 and outer tube 18 of the catheter can be extruded from any thermoplastic that meets friction, stiffness, flexibility and other criteria employed in the design of commercially available percutaneous transluminal angioplasty catheters as known in the art. Preferably, the tubes are extruded from high density polyethylene such as Petrothene 6800-00, which may be obtained from Quantum Chemical Co. of Cincinnati, Ohio. The length of the catheter should be approximately 135 cm, as is typical for conventional percutaneous transluminal coronary angioplasty catheters. The catheter may be marked at a regular interval, 10 cm by way of example, with a radio-opaque marker, as is typically done with conventional catheters known in the art.

The inner tube 14 should have an outer diameter slightly less than that of the distal shoulder 24 of the balloon to facilitate adhesive bonding to the balloon. The internal diameter of the inner tube 14 should preferably be about 0.020 inches to facilitate free passage of a typical guide wire having a diameter of between 0.014 and 0.018 inches. The wall thickness of inner tube 14 should be sufficient to withstand the pressure of the conductive fluid applied in the fluid pathway 20 for balloon inflation, which will typically be less than of four atmospheres. If the inner tube cannot withstand such pressures and collapses, it will bind the guide wire.

Similarly, the outer tube 18 should have an outer diameter slightly less than that of the proximal shoulder 26 of the balloon to facilitate adhesive bonding of the balloon. Balloon and outer tube dimensions should be selected such that the outer diameter of the outer tube 18 is less than 0.050 inches to facilitate steering the catheter through 180° turns in three planes in close proximity without exerting undue transverse pressure on the guide wire which would result in resistance to advancement of the balloon toward the stenosis site. Such flexibility is required to access certain coronary arteries.

Referring again to FIG. 1, the balloon is attached at its distal shoulder 24 to the outer surface of the inner tube 14, and similarly at its proximal shoulder 26 to the outer surface of outer tube 18, by adhesive bonding. Similarly, referring to FIG. 2, the inner tube 14 is attached by adhesive bonding to the inner surface 35 of the channel section 34 of the catheter hub 32. The outer tube 18 is attached by adhesive bonding to the inner surface 37 of the channel section 38 of the catheter hub. The polymeric materials of these surfaces which are bonded together preferably are treated to enhance bonding according to a method which does not change the inherent properties of the materials.

One such way of facilitating high strength bonding of these polymer surfaces is with exposure of the surfaces to activated inert gas, such as activated helium, for a short interval prior to application of an epoxy adhesive. Corona discharge is the preferred form of activation of the inert species for this purpose. The exposure causes a crosslinking of the polymer molecules on the surface of the material exposed, creating high cohesive strength ideal for adhesive bonding. Preferably, only those surfaces meant to be bonded together are exposed. This treatment is known in the art and is detailed in H. Schonhorn, "Surface Treatment of Polymers for Adhesive Bonding", J. Applied Polymer Science, Vol. 11, pp. 1461–1474 (1967), the teachings of which are incorporated by reference.

Figure 3:
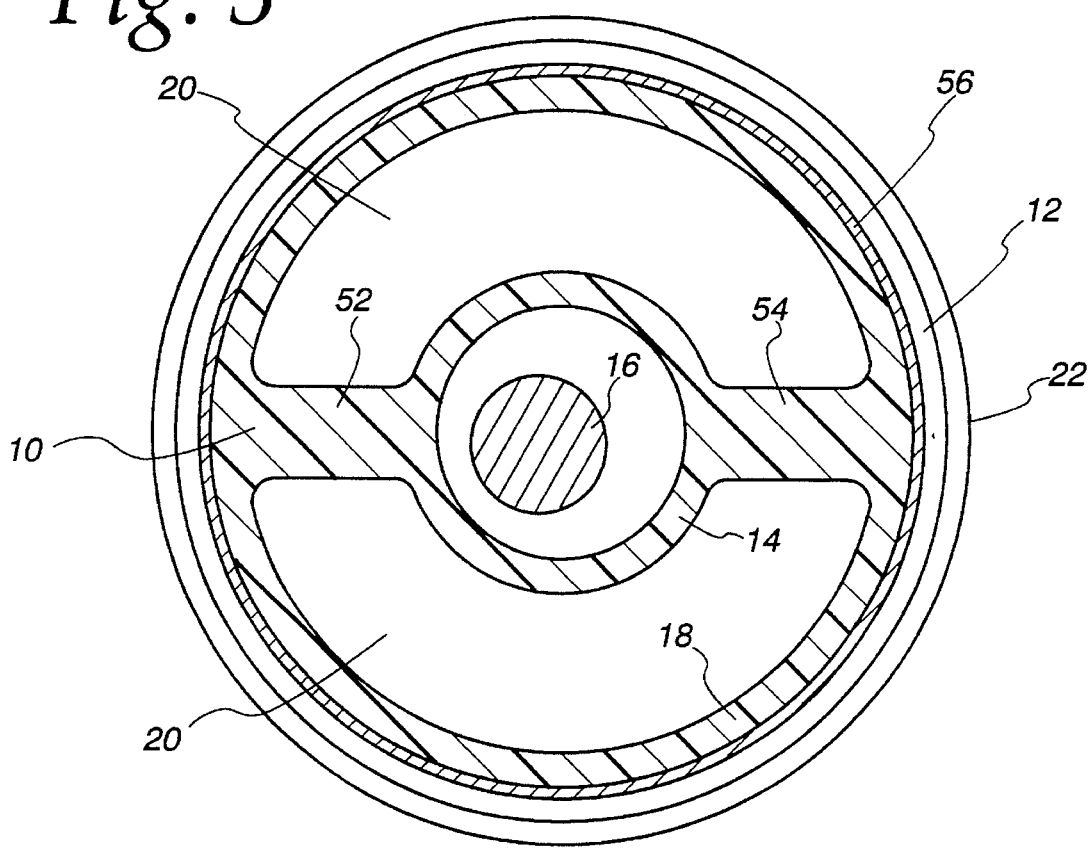
FIG. 3 is a cross-sectional view of an alternative multi-lumen embodiment of the catheter of the present invention.

While the catheter 10 may take the form of two independent tubes, the inner tube 14 and the outer tube 18, one inside the other, such an arrangement need only be a model for the distal and proximal ends of an otherwise multi-lumen extrusion. Turning to FIG. 3, a cross-sectional view of the distal end of the catheter 10 taken along the line 3 in FIG. 1 shows one such possible arrangement of the lumen in a multi-lumen version of the catheter 10. Inner tube 14 and outer tube 18 actually comprise a single solid extrusion having bridging sections 52 and 54 between them. Fluid path 20 now comprises two lumen, one above the bridge and one below the bridge. Epoxy adhesive layer 56, balloon 12, and metalization layer 22 are also shown, but not to scale. Inside inner tube 14 can be seen the guide wire 16.

Figure 4:
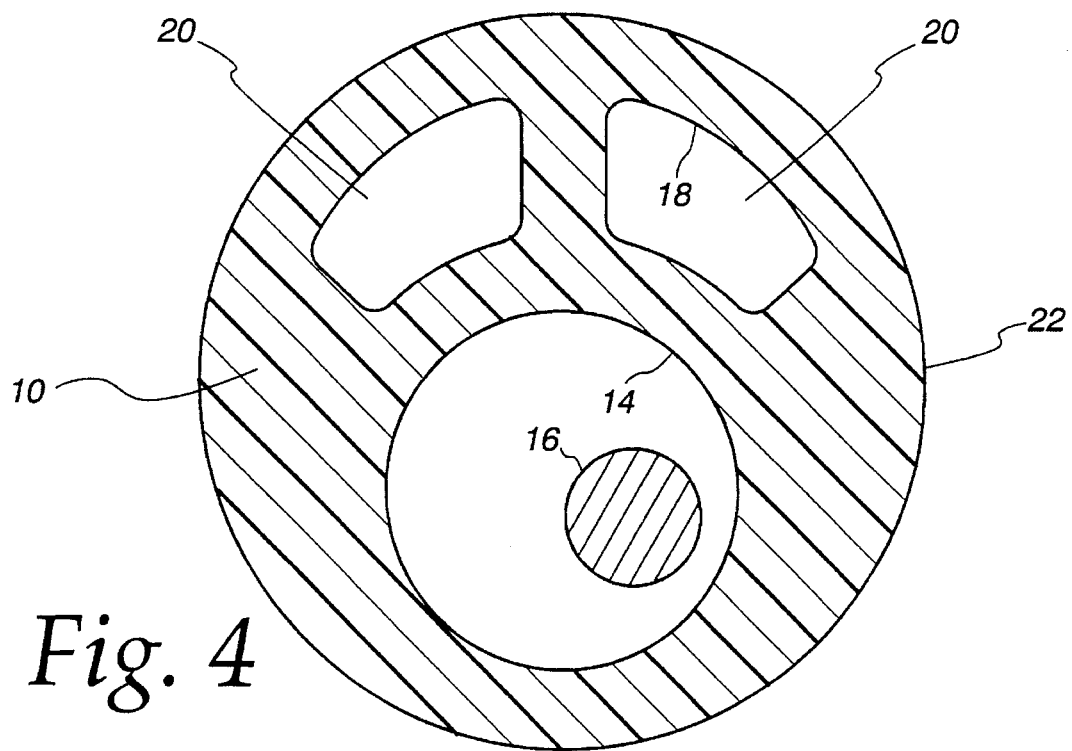
FIG. 4 is a cross-sectional view of another alternative multi-lumen embodiment of the catheter of the present invention.

In an alternative embodiment, the catheter 10 can be formed as a multi-lumen extrusion having a cross-section as shown in FIG. 4, as it would be seen along line bisection the catheter at its mid-point. Here the inner tube 14 and the outer tube 18 have been substantially merged into a single solid multi-lumen extrusion. Furthermore, inner tube 14 and outer tube 18 are no longer concentrically arranged. It is to be understood that this multi-lumen version of the catheter 10 can be so shaped at its distal and proximal ends as to provide the protruding inner tube as shown in FIGS. 1 and 2, and that the catheter hub and balloon can be easily adapted to the non-concentricity of the catheter shaft without any technical difficulty. Also shown are the fluid pathways 20 and the guide wire 16. The metalization layer 22 is shown to scale and therefore appears in the figure to have no thickness.

The catheter should be assembled in the following manner. The extrusion and poling of the balloon, and the extrusion of the multi-lumen shaft of the catheter may first be carried out separately. The catheter hub may be formed and bored according to specifications. The areas of these parts which are to be joined by adhesive are then treated to increase their bondability according to the description above. Subsequently the balloon is bonded with such as epoxy adhesive or the like to the distal end of the catheter. The catheter hub may be bonded to the proximal end of the catheter prior to metalization of the outer surface of the catheter, or may by bonded thereto only after the outer surface has been metalized, since in any case, the catheter hub is not meant to be metalized. Conductive lead 42 may be emplaced in the catheter hub at any time.

Metalization of the outer surface of the catheter, including the outer surface of the balloon, may be achieved by evaporated metal or plasma sputtering techniques, as are commonly known in the art. Such metalizing services are readily available on a commercial basis. It is preferable to inflate the balloon before metalization so that substantially all of its inflated surface area is metalized. Of course, the metalization may also be limited to just the region around the balloon, with a wire embedded in the catheter shaft extrusion connected thereto to provide a conductive path back to the catheter hub. A layer of nickel, copper, gold, silver, or other appropriate conductive metal may be deposited to a thickness in the range of approximately 50 Angstroms to approximately 800 Angstroms. Silver is preferred as the metal layer due to its low resistivity of approximately 1.586 µohm/cm.

After metalization, a conductive wire winding 44 of preferably silver wire may be wrapped around the catheter shaft in intimate conductive contact with the metalized surface. A tail 46 of the winding 44 may be used for connection to an ultrasonic signal source. Thereafter, the winding may be embedded in a coating bead of conductive epoxy resin 48.

Finally, in order to insulate the outer metalized conductive path from contact with the organic tissues of the human body, a conformal coating of Parylene Polymer less than about one micron thick may be applied to the catheter, again with the balloon in the inflated condition. This service is available from Nova Tran Corp., of Clear Lake, Wis.

The balloon transducer of the catheter of the present invention may be powered with an ultrasonic excitation electrical signal source connected to the conductive leads 42 and 46 with the fluid path filled, either nominally or at an increased pressure, with conductive contrast fluid. While the balloon will respond to signals up to 1 GHz, it is preferable to use frequencies in the range of about 10 kHz to about 40 kHz. In clinical use, the power output of the balloon should not exceed 25 watts, otherwise necrosis of the smooth muscle cells may occur. The signal generator used should have a fixed output frequency and a maximum amplitude setting to avoid misuse or inadvertent injury to the patient. The balloon may be driven, by way of example, with a 20 kHz signal with a 500-volt RMS amplitude on a 50% duty cycle of 30 milliseconds at 60 second intervals. In other words, such a drive would deliver 600 cycles of 500 RMS volts for 30 milliseconds, then rest for 30 milliseconds, and this can be done 1000 times for every 60 second interval, after which the drive may be stopped to evaluate progress. The balloon may be driven by any waveform, such as a square wave or a sinusoidal wave, or by pulsed d.c.

In order to excite the piezoelectric balloon, the fluid path 20 is evacuated and then back filled with conductive contrast fluid. The balloon can be excited in either the deflated or inflated state. Silver conductive lead 42 is then in conductive contact with the fluid. A potential applied across the two conductive leads 42 and 46 causes a potential across the thickness of the balloon 12. The potential across the balloon in turn causes dimensional changes in all three planes of the piezoelectric film of the balloon to varying degrees for each plane. As the voltage increases, the magnitude of the deformation increases and if the voltage applied is cyclical, the frequency of the deformation will match the frequency of the applied signal.

Since no conductive fluid is in contact with the distal and proximal shoulders of the balloon where epoxy adhesive bonds the balloon to the inner tube 14 and the outer tube 18, no deformation of the balloon at the bond sites will occur, and these bonds will not be jeopardized by deformation.

The conductive contrast fluid may be provided by a controlled source able to monitor and adjust the fluid pressure applied to the fluid path of the catheter. Preferably, the source is also able to provide an oscillating or periodic pressure to the fluid, for repeated inflation and deflation of the balloon at regular intervals of about 10 milliseconds to about 100 milliseconds, by way of example. Such a device facilitates the cycle of inflation and deflation of the balloon according to the method described below, where deflation allows for flushing of the ablated stenosis material. The device may preferably be a computerized or programmable electronic device with pneumatic control over the applied pressure of the contrast fluid.

Figure 5:
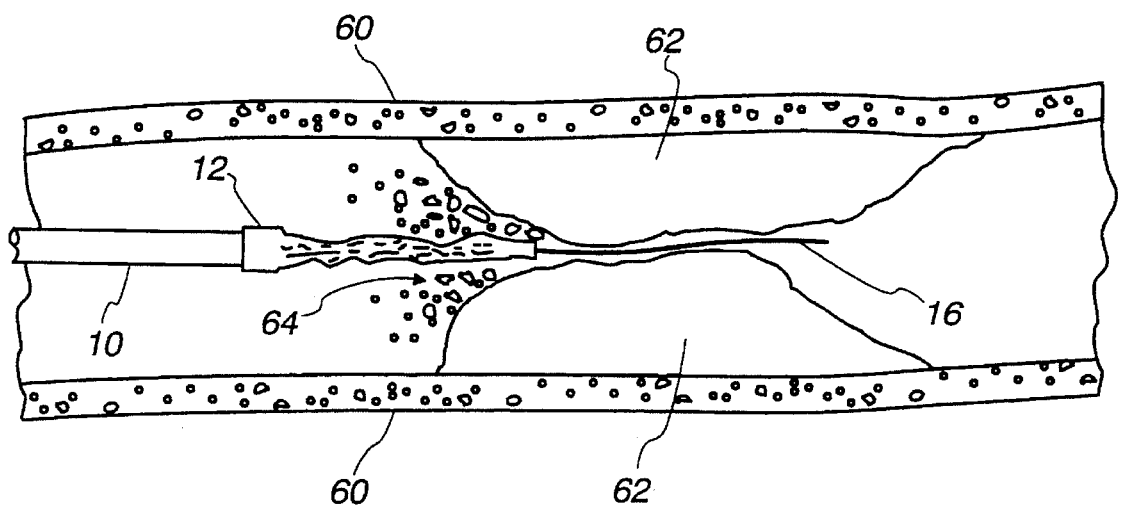
FIG. 5 is a sectional view of a blood vessel stenosis showing the catheter of the present invention in the process of ablating a path across the stenosis.

Turning now to FIG. 5, the angioplasty balloon catheter 10 of the present invention is shown in use in ablating a substantially completely stenosed artery. The arterial wall 60 a buildup 62 of biological material forming the stenosis. The guide wire 16 typically may be pushed through such a stenosis without difficulty because guide wires are very small, very stiff and easy to push. The catheter 10, however, has a much greater profile diameter, and lacks the stiffness of a guide wire so that it cannot be pushed across the stenosis.

When the distal tip of the catheter comes into contact with the stenosis, the balloon, which is in the deflated state, is excited according to the invention with an ultrasonic signal. The balloon material deforms accordingly, with the major axis of deformation being along the axis of the catheter. The amplitude of deformation is small, however the frequency is high, matching the frequency of the ultrasonic signal. This results in a hammering of the tip of the catheter against the stenosis, ablating the biological material thereof. Predominantly, the mechanical impact loosens and breaks up the material, however, ultrasonic energy is also secondarily transmitted to the stenosis via waves in the surrounding blood plasma, which assists in the ablation of the biological material forming the stenosis. The ultrasonic energy is particularly useful in causing the biological material to break up into sufficiently small particle sizes to minimize the risk of downstream embolism or clotting.

Figure 6:
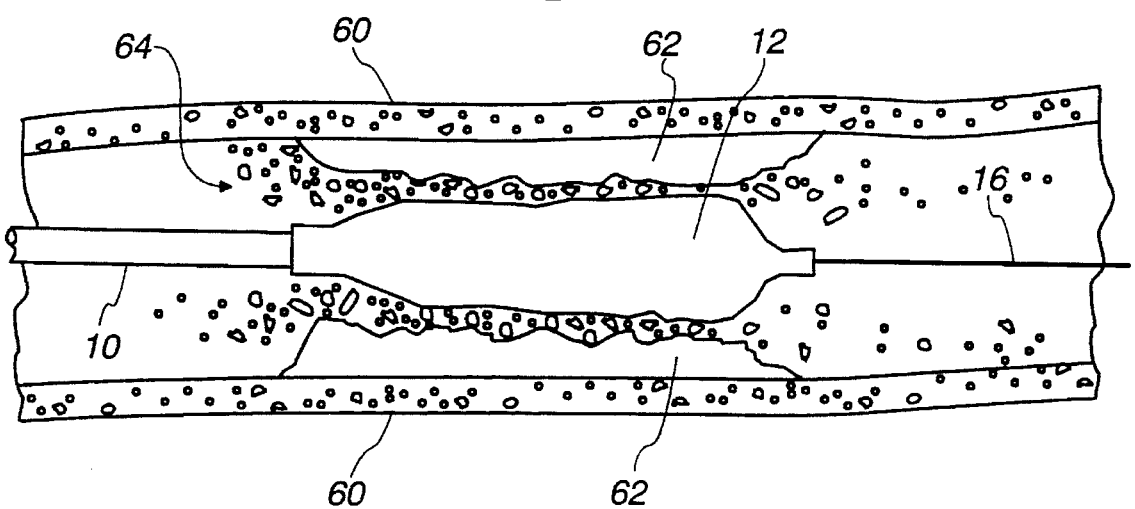
FIG. 6 is a sectional view of a blood vessel stenosis showing the catheter of the present invention after crossing the stenosis and in the process of further ablating the stenosis.

As shown in FIG. 5, the vibration of the balloon, in conjunction with the application of an axial load by the operator, causes the ablation of the stenosis material 64. As a result, the catheter hammers open a path for itself through the stenosis. After the catheter has crossed the stenosis, the pressure of the conductive contrast fluid is increased, preferably by means of a controlled source, to inflate the balloon, as shown in FIG. 6. As the balloon 12 is inflated, the ultrasonic excitation signal is maintained, so that the balloon continues to vibrate. It is contemplated that the balloon may be inflated slowly, by slowly increasing the fluid pressure, or rapidly with an inflation pressure of about four atmospheres, depending on the diameter of the artery, the stenosis material and stenosis size. In either case, the frequency of the excitation signal realizes substantially quicker motion in the form of deformation than the motion of inflation, such that even with rapid inflation, the stenosis material 64 is ablated by ultrasonic vibrations rather than crushed against the arterial wall 60.

A cycle of frequent inflation and deflation during ablation of the stenosis may optimally be employed according to the method of the invention. Apparatus for supplying the inflation pressure should be programmed or otherwise controlled to successively inflate and deflate the balloon in the excited state at a peak pressure of about 4 atmospheres, at a periodicity in the range of about 10 milliseconds to about 100 milliseconds. This periodicity is substantially slower than the frequency of the ultrasonic vibration, allowing for approximately 200 to 2000 vibrations per inflation at an ultrasonic frequency of 20 kHz, for example. At such a periodicity, the periods of balloon deflation permit the ablated stenosis material to be flushed by the flow of blood, and also permit perfusion of blood for downstream supply of oxygen, thereby avoiding ischemia. The perfusion also serves to return the balloon to normal temperature from the anticipated 1° C. or 2° C. anticipated rise in temperature.

The performance of the ultrasonic ablation may be monitored in real-time by means of a fluoroscope, as is commonly practiced in the art in conventional balloon angioplasty. The ablation of the material by repeated inflations of the excited balloon transducer may be performed until substantially all of the stenosis is ablated.

The catheter of the present invention provides a novel means of ablating a stenosis of a coronary artery or any other vessel in the human body. The catheter and the method for using the catheter can be applied to any small profile or even totally occluded stenosis to produce an aperture or completely ablate the stenosis. Ablation has the advantage of reducing the subsequent risk of re-stenosis. Also, the use of ultrasonic energy has the advantage of pulverizing the stenosis into particles too small to create a risk of downstream embolism.

While the invention has been described with reference to a preferred embodiment, it is to be clearly understood by those skilled in the art that the invention is not limited thereto. Accordingly, the scope of the invention is to be interpreted only in conjunction with the appended claims.

What is claimed is:

1. An angioplasty balloon catheter suitable for use in openings a stenosis in a vascular vessel, said catheter having an inflation lumen which connects with an inflatable balloon fabricated at least partially from a polymeric material having piezoelectric properties, and a means of delivering ultrasonic energy to the inflatable balloon via an ultrasonic electrical excitation signal whereby the inflatable balloon can be excited into ultrasonic vibratory states capable of opening the stenosis in the vascular vessel when the excited and vibrating inflatable balloon is in contact with the stenosis.

2. A catheter according to claim 1, wherein the polymeric material comprises polyvinylidene difluoride.

3. A catheter according to claim 1, wherein the polymeric material comprises a combination of at least one polymer selected from the group consisting of polyvinylidene fluoride, polyvinylidene difluoride (PVDF), PVDF/trifluoroethylene, PVDF/tetrafluoroethylene, and polyvinylidene cyanide, and at least one polymer selected from the group consisting of a polyolefin copolymer.

4. A catheter according to claim 3, wherein the polymer comprises PVDF/trifluoroethylene.

5. A catheter according to claim 4, wherein the polyolefin copolymer is polyethylene terphthalate.

6. A catheter according to claim 3, wherein the polymer comprises PVDF and the polyolefin copolymer is polyethylene terephthalate.

7. A catheter according to claim 3, wherein the polymer comprises polyvinylidene cyanide.

8. A catheter according to claim 1, wherein the ultrasonic electrical excitation signal is applied across the thickness of the polymeric material of the inflatable balloon.

9. A catheter according to claim 8, further including a source of fluid pressure coupled to the inflation lumen for transferring a conductive fluid through the inflation lumen to the interior of the inflatable balloon, whereby the inflatable balloon can be inflated.

10. A catheter according to claim 9, wherein the inflatable balloon includes a contiguous layer of a conductive metal extending over the polymeric material.

11. A catheter according to claim 9 further having a contiguous layer of a conductive metal forming an outer surface of the catheter, including the inflatable balloon.

12. A catheter according to claim 12, wherein the layer of the conductive metal forming the outer surface of the catheter is silver or gold.

13. A catheter according to claim 12 further having a flexible coating of an insulating material surrounding the layer of the conductive metal.

14. An angioplasty balloon catheter suitable for use in opening a stenosis in a human blood vessel, said catheter comprising:

a flexible catheter shaft having at least two lumens, including a first lumen for accommodating a guide wire and a second lumen for transporting a conductive fluid, and having a proximal end and a distal end for insertion into the human blood vessel containing the stenosis, an inflatable balloon fabricated at least partially from a polymeric material having piezoelectric properties, located at the distal end of the shaft, and attached so as to seal the second lumen at the proximal end of the catheter shaft, such that the balloon is disposed to inflate with conductive fluid transported into the second lumen, and a continuous layer of a conductive metal forming an outer surface of catheter, including the balloon, whereby the balloon can be excited into ultrasonic vibratory states capable of opening the stenosis in the human blood vessel when the excited and vibrating balloon is in contact with the stenosis.

15. A catheter according to claim 14 further having a flexible coating of an insulating polymeric material surrounding the continuous layer of the conductive metal.

16. A catheter according to claim 14, wherein the piezoelectric polymeric material has a thickness in a range of about 9 microns to about 56 microns when the balloon is not inflated.

17. A catheter according to claim 14, wherein the balloon has a length in a range of about 20 millimeters to about 25 millimeters.

18. A catheter according to claim 14, wherein the balloon has a burst pressure of at least ten atmospheres.

19. A catheter according to claim 14, wherein the balloon has an inflated profile diameter in the range of about 2 millimeters to about 4 millimeters.

20. A catheter according to claim 19, wherein the catheter shaft has a diameter of less than about 0.050 inches.

21. A catheter according to claim 14, wherein the balloon comprises polyvinylidene difluoride.

22. A catheter according to claim 21, wherein the layer of the conductive metal is silver or gold.

23. A catheter according to claim 22 further having at the proximal end of the shaft a catheter hub having a sealable opening for introducing the conductive fluid into the second lumen and having a conductive lead disposed to intimate conductive contact with the conductive fluid when introduced into the second lumen, for connection to a source of an ultrasonic electrical excitation signal.

24. A catheter according to claim 23 further having a conductive winding wrapped in intimate conductive contact with the layer of conductive metal near the proximal end of the catheter, the winding further having a second conductive lead for connection to the source of the ultrasonic electrical excitation the source of the ultrasonic electrical excitation signal.

25. A catheter according to claim 14, wherein the balloon comprises a combination of at least one polymer selected from the group consisting of polyvinylidene fluoride, polyvinylidene difluoride (PVDF), PVDF/trifluoroethylene, PVDF/tetrafluoroethylene, and polyvinylidene cyanide, and at least one polymer selected from the group consisting of a polyolefin copolymer.

26. A catheter according to claim 25, wherein the balloon comprises a combination of PVDF/trifluoroethylene and the polyolefin copolymer.

27. A catheter according to claim 26, wherein the polyolefin copolymer is polyethylene terephthalate.

28. A catheter according to claim 25, wherein the balloon comprises a combination of PVDF and the polyolefin copolymer and wherein the polyolefin copolymer is polyethylene terephthalate.

29. A catheter according to claim 25, wherein the balloon comprises a combination of polyvinylidene cyanide and the polyolefin copolymer.

* * * * *

UNITED STATES PATENT AND TRADEMARK OFFICE
CERTIFICATE OF CORRECTION

PATENT NO. : 5,609,606
DATED : March 11, 1997
INVENTOR(S) : Matthew O'Boyle

It is certified that error appears in the above-indentified patent and that said Letters Patent is hereby corrected as shown below:

Claim 1, Column 11, Line 29, change "openings" to --opening--

Claim 5, Column 11, Line 51, change "terphthalate" to --terephthalate--

Claim 12, Column 12, Line 4, change "12" (second occurrence) to --11--

Claim 24, Column 12, Line 64, after "excitation" (first occurrence), delete "the source of the ultrasonic electrical excitation"

Signed and Sealed this

First Day of July, 1997

Attest:

BRUCE LEHMAN

Attesting Officer

Commissioner of Patents and Trademarks